(12) United States Patent  
Choi et al.

(10) Patent No.: US 8,509,508 B2
(45) Date of Patent: Aug. 13, 2013

(54) MEDICAL IMAGING SYSTEM AND IMAGE PROCESSING METHOD

(75) Inventors: Doo Hyun Choi, Gyeonggi-do (KR); Jae Yoon Shim, Seoul (KR)

(73) Assignee: Samsung Medison Co., Ltd., Kangwon-Do (KR)

( * ) Notice: Subject to any disclaimer, the term of this patent is extended or adjusted under 35 U.S.C. 154(b) by 277 days.

(21) Appl. No.: 13/103,513

(22) Filed: May 9, 2011

(65) Prior Publication Data

US 2011/0293152 A1     Dec. 1, 2011

(30) Foreign Application Priority Data

Jun. 1, 2010 (KR) .......................... 10-2010-0051651
Sep. 2, 2010 (KR) .......................... 10-2010-0085984

(51) Int. Cl.
*G06K 9/00* (2006.01)
(52) U.S. Cl.
USPC ........................... 382/128; 382/284; 600/437
(58) Field of Classification Search
USPC ............... 382/100, 128, 129, 130, 131, 132, 382/133, 134, 162, 168, 173, 181, 209, 219, 382/232, 254, 274, 276, 284, 294, 305, 312; 706/16; 600/443, 437, 425; 378/4, 21; 1/1
See application file for complete search history.

(56) References Cited

U.S. PATENT DOCUMENTS

| | | | | |
|---|---|---|---|---|
| 6,708,055 B2* | 3/2004 | Geiser et al. | ................. | 600/425 |
| 6,942,618 B2* | 9/2005 | Simopoulos | ................. | 600/437 |
| 7,187,790 B2* | 3/2007 | Sabol et al. | ................. | 382/128 |
| 7,490,085 B2* | 2/2009 | Walker et al. | ................. | 1/1 |
| 7,654,958 B2* | 2/2010 | Byrd et al. | ................. | 600/443 |
| 2006/0112033 A1* | 5/2006 | Vion et al. | ................. | 706/16 |

FOREIGN PATENT DOCUMENTS

| | | |
|---|---|---|
| EP | 2 145 580 A1 | 1/2010 |
| KR | 10-2007-0039230 A | 11/2007 |
| KR | 10-2010-0007819 A | 1/2010 |
| WO | WO 01/80739 A1 | 11/2001 |

OTHER PUBLICATIONS

Lee, Mark E., et al., "A Note on the Use of Nonlinear Filtering in Computer Graphics", IEEE Computer Graphics and Applications, May 1, 1990, pp. 23-29, vol. 10, No. 3, IEEE Service Center, New York, NY.
Extended European Search Report, issued in European Patent Application No. 11 163 288.1, dated Aug. 24, 2011.
Korean Office Action issued in Korean Application No. 10-2010-0085984 mailed Sep. 23, 2011.

* cited by examiner

*Primary Examiner* — Seyed Azarian
(74) *Attorney, Agent, or Firm* — McDermott Will & Emery LLP

(57) ABSTRACT

A medical imaging system and an image processing method for producing an optimized image from an input image are provided. The medical imaging system comprises: a parameter accumulator configured to accumulate a preset number of basic parameters; a parameter determiner configured to produce new reference parameters based on current reference parameters and the accumulated basic parameters to replace the current reference parameters with the new reference parameters; an image processor configured to process an input image to generate an optimized image according to an image processing algorithm based on the reference parameters sent from the parameter determiner; and a controller configured to control overall operation of the medical imaging system.

16 Claims, 2 Drawing Sheets

MEDICAL IMAGING SYSTEM AND IMAGE PROCESSING METHOD

TECHNICAL FIELD

The present disclosure relates to a medical imaging system and image processing method and, more particularly, to a medical imaging system and image processing method for automatically generating an optimized image from an acquired object image in a medical imaging system, such as an ultrasonic diagnostic system, based on user preference or system usage history.

BACKGROUND

Medical imaging systems are used in a wide range of applications to process and display images of an object. Herein, an ultrasonic diagnostic system will be described as an example of a medical imaging system.

Ultrasonic diagnostic systems are used in a wide range of medical applications due to non-invasive and non-destructive characteristics thereof.

An ultrasonic diagnostic system must obtain an optimized ultrasound image of a target so that accurate diagnosis can be performed based on the ultrasound image. Accordingly, users need to adjust a variety of image parameters, such as gain, time gain compensation (TGS), dynamic range (DR) and reject, which correspond to brightness, contrast, etc. of the ultrasound image displayed on a monitor of the system. However, since it is very inconvenient to adjust such parameters whenever the ultrasonic diagnostic system is used, investigations have been made in the art to achieve automatic adjustment of such parameters.

For example, a conventional ultrasonic diagnostic system is configured to store predetermined reference parameters and to process an input image according to a predetermined image processing algorithm based on the reference parameters to generate an optimized image. One example of this system is disclosed in Korean Patent No. 748858.

However, since such a conventional ultrasonic diagnostic system uses reference parameters preset by system manufacturers, users cannot change the reference parameters. That is, although the conventional ultrasonic diagnostic system can automatically process images based on the preset reference parameters, the reference parameters cannot be changed by users as needed. Thus, in order to obtain images processed based on desired parameters other than the preset reference parameters, the users must manually reset the parameters whenever using the system.

That is, such a conventional medical imaging system including the conventional ultrasonic diagnostic system has predetermined algorithms for image processing to automatically process input images based on preset reference parameters, but has no mechanism to provide optimized parameters changed from existing reference parameters based on user preference.

SUMMARY

The present disclosure provides a medical imaging system and image processing method for automatically generating an optimized image from an acquired object image in the medical imaging system, such as an ultrasonic diagnostic system, based on user preference or system usage history.

In accordance with an aspect of the present invention, a medical imaging system for producing an optimized image from an input image is disclosed. The system includes: a parameter accumulator configured to accumulate a preset number of basic parameters; a parameter determiner configured to produce new reference parameters based on current reference parameters and the accumulated basic parameters to replace the current reference parameters with the new reference parameters; an image processor configured to process an input image to generate an optimized image according to an image processing algorithm based on the reference parameters sent from the parameter determiner; and a controller configured to control overall operation of the medical imaging system.

The parameter determiner may calculate an arithmetic average of at least some of the accumulated basic parameters and produce new reference parameters based on the current reference parameters and the arithmetic average.

Each of the new reference parameters may be determined by the following equation:

$$R_0' = \alpha R_n + (1-\alpha) R_0$$

where $R_0'$ is a new reference parameter, $R_0$ is a current reference parameter, $R_n$ is an arithmetic average, and $0 \leq \alpha \leq 1$.

The arithmetic average may be an arithmetic average of the accumulated basic parameters except for a certain percentage of each of the top and bottom basic parameters.

The parameter determiner may produce the new reference parameters and all of the accumulated basic parameters may be deleted from the parameter accumulator, when the number of basic parameters accumulated in the parameter accumulator reaches the preset number of basic parameters.

The parameter accumulator may store parameters corresponding to the optimized image as the basic parameters, whenever the optimized image is stored by a user.

The medical imaging system may be an ultrasonic diagnostic system, and the parameters may include at least one of gain, time gain compensation and dynamic range.

The reference parameters may be determined on a per user basis, a per user probe basis, and/or a per treatment-target basis.

In accordance with another aspect of the present invention, an image processing method of a medical imaging system processing an input image of an object to generate an optimized image based on reference parameters is disclosed. The method includes steps of: accumulating basic parameters; determining whether the number of accumulated basic parameters reaches a preset number; if the number of accumulated basic parameters reaches the preset number, producing new reference parameters based on current reference parameters and the accumulated basic parameters to replace the current reference parameters with the new reference parameters; and processing an input image of an object to generate an optimized image according to an image processing algorithm using the reference parameters. Here, at the step of determining, if the number of accumulated basic parameters does not reach the preset number, then the step of processing is performed.

The step of producing new reference parameters may include calculating an arithmetic average of at least some of the accumulated basic parameters; and producing the new reference parameters based on the current reference parameters and the arithmetic average.

The reference parameters may be restored to default settings which are initially set in the medical imaging system.

BRIEF DESCRIPTION OF THE DRAWINGS

The figures depict one or more implementations in accordance with the present disclosure, by way of example only.

DETAILED DESCRIPTION

Exemplary embodiments of the present disclosure will now be described in detail with reference to the accompanying drawings. It should be noted that the following description is provided for illustrative purposes only and does not limit the scope of the following claims.

Figure 1:
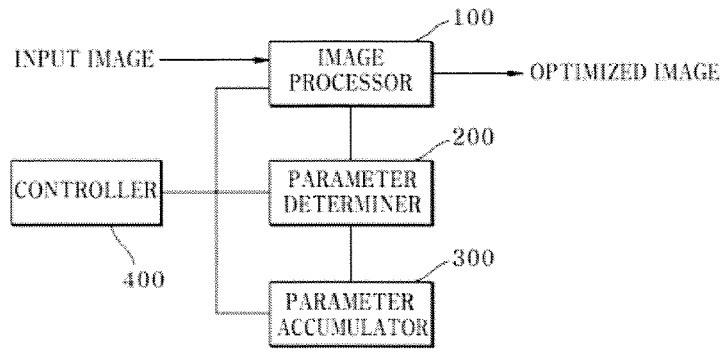
FIG. 1 is a block diagram of a medical imaging system in accordance with an embodiment of the present disclosure.
Figure 2:
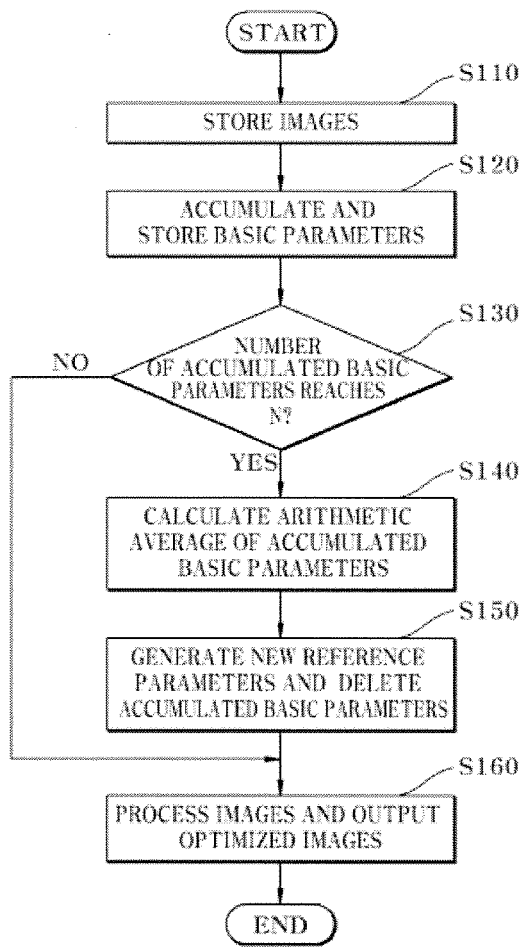
FIG. 2 is a flow chart of an image processing method in accordance with an embodiment of the present disclosure.
Figure 3:
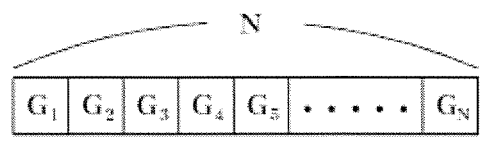
FIG. 3 illustrates a memory configuration of a parameter accumulator in accordance with an embodiment of the present disclosure.

FIG. 1 is a block diagram of a medical imaging system in accordance with an embodiment of the present disclosure. FIG. 2 is a flow chart of an image processing method in accordance with an embodiment of the present disclosure. FIG. 3 illustrates a memory configuration of a parameter accumulator in accordance with an embodiment of the present disclosure.

Referring to FIG. 1, the medical imaging system according to the embodiment includes a parameter accumulator 300, a parameter determiner 200, an image processor 100, and a controller 400. The parameter accumulator 300 accumulates a preset number of basic parameters. The parameter determiner 200 produces new reference parameters based on current reference parameters and the accumulated basic parameters. The image processor 100 produces an optimized image from an input image according to an image processing algorithm based on the new reference parameters from the parameter determiner 200. The controller 400 controls overall operation of the medical imaging system.

The medical imaging system will be described in more detail with reference to FIGS. 1 to 3.

The parameter accumulator 300, the parameter determiner 200 and the image processor 100 are operated under control of the controller 400.

The medical imaging system may operate in an optimized image mode. Referring to FIG. 1, in the optimized image mode, the medical imaging system automatically processes an input image to generate an optimized image according to a predetermined image processing algorithm using reference parameters. That is, when a user selects the optimized image mode of the medical imaging system, the image processor 100 automatically processes the input image to generate an optimized image based on the reference parameters. Although the medical imaging system uses initial values at the first time, which are preset by a system manufacturer, as the reference parameters, the system may use new reference parameters which are generated based on a system usage history, as described below. Examples of the reference parameters may include image parameters, which correspond to image brightness or contrast, such as gain, time gain compensation (TGC), dynamic range (DR), or reject.

If an optimized image output from the image processor 100 is stored by a user in operation 110, the parameter accumulator 300 accumulates current parameters, which are set to correspond to the optimized image, as basic parameters $G_1$, $G_2$, $G_3$, etc., in a memory as shown in FIG. 3, in operation 120. The current parameters may be reference parameters which are currently set in the medical imaging system, or parameters which are manually set by a user. The medical imaging system determines the optimized image stored by the user as the user's image preference and stores parameters set to correspond to the optimized image as the basic parameters in the parameter accumulator 300.

In operation 130, the controller 400 determines whether the number of basic parameters $G_1$, $G_2$, $G_3$, etc. stored in the parameter accumulator 300 reaches a preset number N. If the number of basic parameters reaches the preset number N, the process proceeds to the following operation 140. If not, the reference parameters maintain existing reference parameter values and operation 160 is performed. The preset number N may be a default value, which is initially preset in the medical imaging system, or a value of 1000, 2000 or the like, which is arbitrarily set by a user.

If it is determined in operation 130 that the number of accumulated basic parameters $G_1$, $G_2$, $G_3$, etc. reaches the preset number N, the parameter determiner 200 calculates an arithmetic average of at least some of the accumulated basic parameters, in operation 140. The arithmetic average may be an arithmetic average of the accumulated basic parameters except for a certain percentage of each of the top and bottom basic parameters, for example, except for the top 5% and bottom 5% of the basic parameters. In this case, the parameter determiner 200 may obtain the average and standard deviation of the overall basic parameters and perform the above-mentioned operation upon the basic parameters except for a predetermined percentage of the top and bottom of the normal distribution (Gaussian distribution).

In operation 150, the parameter determiner 200 produces new reference parameters based on the current reference parameters and the obtained arithmetic average, and the controller 400 deletes the basic parameters from the parameter accumulator 300. Accordingly, the new reference parameters are used in the optimized image mode. The current reference parameters may be default reference parameters which are initially preset in the medical imaging system, or reference parameters which are updated after the initial reference parameters are set. The new reference parameters may be determined as follows:

$$R_0' = \alpha R_n + (1-\alpha) R_0$$

(where $R'_0$ is a new reference parameter, $R_0$ is a current reference parameter, $R_n$ is an arithmetic average, and $0 \leq \alpha \leq 1$).

α is a constant for determining which of the current reference parameter and the arithmetic average has a greater weight. A greater α means that the arithmetic average of the accumulated basic parameters has a greater weight.

In operation 160, the image processor 100 processes an input image to generate an optimized image according to a predetermined image processing algorithm using the reference parameters. If the determination result is 'No' in operation 130 and the process proceeds to operation 160, the image processor 100 performs image processing based on the existing reference parameters. However, if the determination result is 'Yes' in operation 130 and the operations 140, 150 and 160 are sequentially performed, the image processor 100 receives the new reference parameters from the parameter determiner 200 and processes the input image to generate the optimized image according to the predetermined image processing algorithm using the new reference parameters.

The medical imaging system and image processing method may be applied to a variety of medical imaging devices including an ultrasonic diagnostic system.

The medical imaging system may operate in the optimized image mode on a per user basis, on a per user-probe basis, and/or on a per treatment-target basis. Accordingly, the reference parameters may be determined on a per user basis, on a per user-probe basis, and/or on a per treatment-target basis.

In one embodiment, the reference parameters may be restored to the default settings, which are initially set in the medical imaging system, according to, for example, user selection, predetermined time setup or predetermined conditions which are set in the medical imaging system.

As such, the medical imaging system may generate the optimized image suited to user preference by producing new reference parameters used for the optimized image mode whenever the number of basic parameters accumulated in the parameter accumulator 300 reaches the preset number N.

Although the parameter determiner 200 and the parameter accumulator 300 are described as being separately provided in this embodiment, the parameter determiner 200 and the parameter accumulator 300 may be incorporated into a single entity.

As apparent from the above description, the medical imaging system and image processing method according to the embodiments automatically generates optimized images from acquired object images on a per user basis and/or on a per treatment-target basis by automatically setting reference parameters applied to the image processing algorithm according to the user preference or system usage history.

While the foregoing has described what are considered to be the best mode and/or other examples, it is understood that various modifications may be made therein, that the subject matter disclosed herein may be implemented in a variety of different ways, and that the present disclosure may be applied to numerous applications, only some of which have been described herein. The following claims should be considered to cover all applications, modifications and variations within the true scope of the present disclosure.

What is claimed is:

1. A medical imaging system for producing an optimized image from an input image of an object, comprising:
   a parameter accumulator configured to accumulate a preset number of basic parameters;
   a parameter determiner configured to produce new reference parameters based on current reference parameters and the accumulated basic parameters to replace the current reference parameters with the new reference parameters;
   an image processor configured to process an input image to generate an optimized image according to an image processing algorithm based on the reference parameters sent from the parameter determiner; and
   a controller configured to control overall operation of the medical imaging system;
   wherein the medical imaging system is an ultrasonic diagnostic system, and the parameter comprises at least one of gain, time gain compensation and dynamic range.

2. The system of claim 1, wherein the parameter determiner calculates an arithmetic average of at least some of the accumulated basic parameters and produces the new reference parameters based on the current reference parameters and the arithmetic average.

3. The system of claim 2, wherein the new reference parameters are determined by the following Equation:

$$R_0' = \alpha R_n + (1-\alpha) R_0$$

where $R_0'$ is a new reference parameter, $R_0$ is a current reference parameter, $R_n$ is an arithmetic average, and $0 \leq \alpha \leq 1$.

4. The system of claim 3, wherein the arithmetic average is an arithmetic average of the accumulated basic parameters except for a certain percentage of each of the top and bottom basic parameters.

5. The system of claim 1, wherein the parameter determiner produces the new reference parameters and all of the accumulated basic parameters may be deleted from the parameter accumulator when the number of basic parameters accumulated in the parameter accumulator reaches the preset number of basic parameters.

6. The system of claim 5, wherein the parameter accumulator stores parameters corresponding to the optimized image as the basic parameters whenever the optimized image is stored by a user.

7. The system of claim 1, wherein the reference parameters are determined on a per user basis, a per user probe basis, and/or a per treatment-target basis.

8. The system of any one of claim 1, wherein the reference parameters are restored to default settings which are initially set in the medical imaging system.

9. An image processing method of a medical imaging system processing an input image of an object to generate an optimized image based on reference parameters, the method comprising:
   accumulating basic parameters;
   determining whether the number of accumulated basic parameters reaches a preset number;
   if the number of accumulated basic parameters reaches the preset number, producing new reference parameters based on current reference parameters and the accumulated basic parameters to replace the current reference parameters with the new reference parameters;
   and processing an input image of an object to generate an optimized image according to an image processing algorithm using the reference parameters, wherein at the step of determining, if the number of accumulated basic parameters does not reach the preset number, then the step of processing is performed;
   wherein the method is used in an ultrasonic diagnostic system and the parameter is at least one of gain, time gain compensation, and dynamic range.

10. The method of claim 9, wherein the step of producing new reference parameters comprises:
    calculating an arithmetic average of at least some of the accumulated basic parameters; and
    producing the new reference parameters based on the current reference parameters and the arithmetic average.

11. The method of claim 10, wherein the new reference parameter is determined by the following equation:

$$R_0' = \alpha R_n + (1-\alpha) R_0$$

where $R_0'$ is a new reference parameter, $R_0$ is a current reference parameter, $R_n$ is an arithmetic average, and $0 \leq \alpha \leq 1$.

12. The method of claim 11, wherein the arithmetic average is an arithmetic average of the accumulated basic parameters except for a certain percentage of each of the top and bottom basic parameters.

13. The method of claim 9, wherein, if the number of accumulated basic parameters reaches the preset number, the new reference parameters are generated and the accumulated basic parameters are deleted.

14. The method of claim 13, wherein the step of accumulating the basic parameters is performed when the optimized image is stored.

15. The method of claim 9, wherein the reference parameters are determined on a per user basis, on a per user probe basis, and/or on a per treatment-target basis.

16. The method of any one of claim 9, wherein the reference parameters are restored to default settings which are initially set in the medical imaging system.

* * * * *